United States Patent [19]

Kanmacher et al.

[11] Patent Number: 4,925,943

[45] Date of Patent: May 15, 1990

[54] 2-(2-AMINOBENZYL OR 2-NITROBENZYL)-1,2,3,4-TETRAHYDROISOQUINOLINE DERIVATIVES

[76] Inventors: Isabelle Kanmacher, 12, rue Hardouin Mansart, Mittelhausbergen, F-67200 Strasbourg; Jean-Francois Stambach, 10, rue d'Andlau, F-67000 Strasbourg; Louis Jung, 205, route d'Oberhausbergen, F-67200 Strasbourg; Christa Schott, 7, square du Chateau, F-67300 Schiltigheim; Jean-Claude Stoclet, 13, boulevard Jean-Sebastian Bach, F-67000 Strasbourg; Christiane Heitz, 3, rue des Bouvreuils, F-67100 Strasbourg, all of France

[21] Appl. No.: 124,793

[22] PCT Filed: Mar. 4, 1987

[86] PCT No.: PCT/FR87/00054

§ 371 Date: Jan. 5, 1988

§ 102(e) Date: Jan. 5, 1988

[87] PCT Pub. No.: WO87/05295

PCT Pub. Date: Sep. 11, 1987

[30] Foreign Application Priority Data

Mar. 5, 1986 [FR] France ................. 86 03201

[51] Int. Cl.$^5$ ......................... C07D 217/04
[52] U.S. Cl. ................. 546/149; 544/245; 544/246; 546/90; 546/146; 546/148
[58] Field of Search ........... 546/149, 148, 146, 90; 514/307

[56] References Cited

U.S. PATENT DOCUMENTS 3,542,782 11/1970 Houlihan et al. ............ 544/246

FOREIGN PATENT DOCUMENTS

| 7607 | 1/1970 | France . |
| 2054483 | 4/1971 | France . |
| 2059979 | 6/1971 | France . |
| WO87/05295 | 9/1987 | France .............. 546/149 |

OTHER PUBLICATIONS

Pictet et al., "Chem. Ber.", vol. 44, 1911, pp. 2036–2045.
Späth et al., "Chem. Ber.", vol. 72, 1939, pp. 334–338.

*Primary Examiner*—Richard L. Raymond
*Assistant Examiner*—James H. Turnipseed
*Attorney, Agent, or Firm*—Young & Thompson

[57] ABSTRACT

Derivatives of 2-(2-aminobenzyl or 2-nitrobenzyl)-1,2,3,4-tetrahydroisoquinoline of the formula

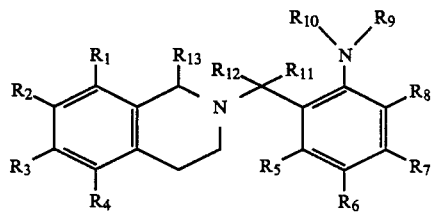

in which each of substituents $R_1$, $R_2$, $R_3$, $R_4$, $R_5$, $R_6$, $R_7$ or $R_8$ may represent either a hydrogen atom, a straight or branched chain alkyl group, a straight or branched chain alkoxy group, a hydroxy group or corresponding esters, a phenoxy group, a benzyloxy group, a methylenedioxy bridge (—O—CH$_2$—O—) when this substituent is connected with an adjacent carbon, a halogen, a nitro group, an amine function corresponding to primary or secondary or tertiary amine, or quarternary ammonium;

each of substituents $R_9$ or $R_{10}$ may represent either a hydrogen atom, a straight or branched chain alkyl group, an arylalkyl group, an amine function corresponding to primary or secondary or tertiary amine or quarternary ammonium, or may each be oxygen atoms;

each of substituents $R_{11}$ or $R_{12}$ may represent either a hydrogen atom, or a straight or branched chain alkyl group; $R_{11}$ and $R_{12}$ may also together form an oxygen atom; $R_{13}$ may represent either a hydrogen atom, or a straight or branched chain alkyl group. These compounds have α-adrenergic activity, and more particularly either α1 or α2 adrenergic specificity.

2 Claims, 3 Drawing Sheets

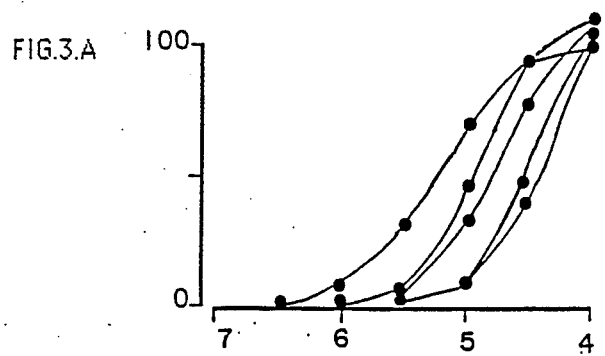
FIG.3.A
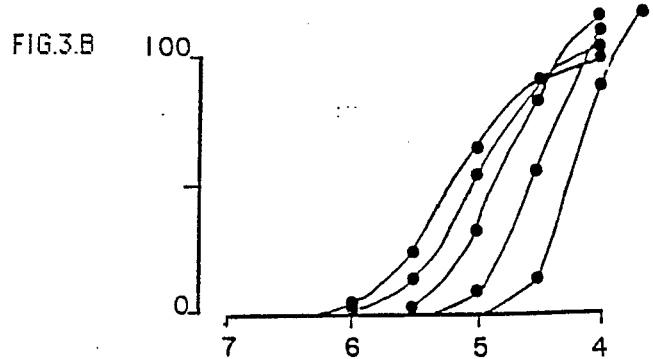
FIG.3.B
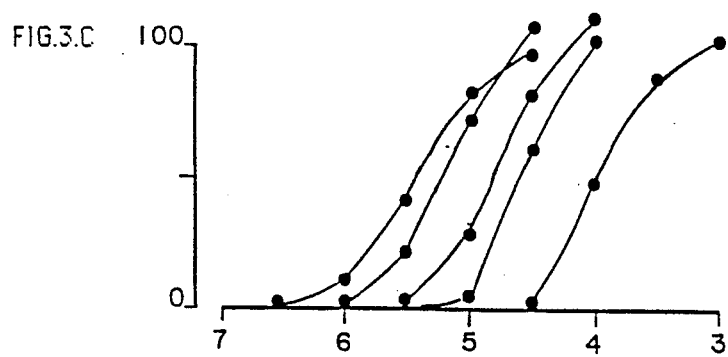
FIG.3.C

2-(2-AMINOBENZYL OR 2-NITROBENZYL)-1,2,3,4-TETRAHYDROISOQUINOLINE DERIVATIVES

The present invention concerns new 2-(2-aminobenzyl or 2-nitrobenzyl)-1,2,3,4-tetrahydroisoquinoline derivatives, as well as their salts, processes for their preparation, their pharmacological α2-adrenergic blocking activity, and pharmaceutical compositions containing same.

At present, numerous α-adrenolytic molecules have been discovered. However, few among them have a good α2-adrenergic selectivity. For example, yohimbine, currently used as an α2 blocking reference substance, although having only slight affinity for α1 receptors, has other effects which limit its therapeutic use.

The present invention is thus directed toward effecting specific α2 blocking molecules. The results of this work have permitted, by modifying 2-benzylisoquinoline (having a chemical structure different than that of yohimbine), selecting new compounds with α2 adrenergic affinity.

The substances according to the invention also have the advantage of being more water-soluble, more stable and less expensive to make than yohimbine.

The invention has for an object 2-(2-aminobenzyl or 2-nitrobenzyl)-1,2,3,4-tetrahydroisoquinoline derivatives, as well as their mineral or organic acid addition salts, corresponding to the general formula I:

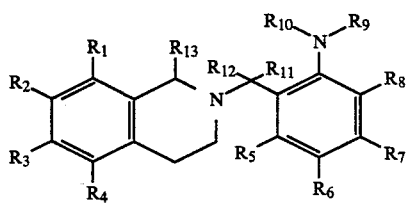

in which each of substituents $R_1$, $R_2$, $R_3$, $R_4$, $R_5$, $R_6$, $R_7$ or $R_8$ may represent either a hydrogen atom, a straight or branched chain alkyl group preferably having 1 to 4 carbon atoms, a straight or branched chain alkoxy group preferably having 1 to 4 carbon atoms, a hydroxy group or corresponding esters, a phenoxy group, a benzyloxy group, a methylenedioxy (—O—CH$_2$—O—) bridge when this substituent is connected with an adjacent carbon, a halogen, a nitro group, or an amine function corresponding to primary, secondary or tertiary amino, or quaternary ammonium;

each of substituents $R_9$ or $R_{10}$ may represent either a hydrogen atom, a straight or branched chain alkyl group preferably having 1 to 4 carbon atoms, an arylalkyl group, an amine function corresponding to primary, secondary or tertiary amino or quaternary ammonium, or may both be an oxygen atom; each of substituents $R_{11}$ or $R_{12}$ may represent either a hydrogen atom, or a straight or branched chain alkyl group preferably having 1 to 4 carbon atoms;

$R_{11}$ and $R_{12}$ may also together form an oxygen atom;

$R_{13}$ may represent either a hydrogen atom, or a straight or branched chain alkyl group preferably having 1 to 4 carbon atoms;

with the exclusion of the compound where $R_1=R_4=R_5=R_7=R_8=R_9=R_{10}=R_{11}=R_{12}=R_{13}=$H, $R_2=R_3=OCH_3$ and $R_6=CH_3$.

In the general formula I and hereinafter, the term alkyl radical preferably containing 1 to 4 carbon atoms designates, for example, a methyl radical and the term alkoxy radical represents, for example, methoxy. The halogen atom may be either fluorine, chlorine, bromine or iodine.

The substituents on tetrahydroisoquinoline may be at any position on the benzenic nucleus, but preferably at position 6 and 7 or 6 or 7, which corresponds to $R_3$ and $R_2$.

The substituents on the 2-aminobenzyl or 2-nitrobenzyl group may be at any position on the benzene nucleus, but preferably at the para and meta or para or meta positions, which correspond to $R_6$ and $R_7$.

The mineral or organic acid addition salts may for example be salts formed with hydrochloric acid.

Among the products according to the invention, there can be mentioned the derivatives corresponding to formula I above, as well as their addition salts with mineral or organic salts, characterized in that, in the said formula I, each of the substituents $R_9$ or $R_{10}$ may represent either a hydrogen atom, or a methyl group, or may each be an oxygen atom; each of the substituents $R_2$ or $R_3$ may represent a hydrogen atom, or a methoxy group, or a benzyloxy group; each of substituents $R_6$ or $R_7$ may represent either a hydrogen atom, or a methoxy group, or a halogen; $R_2$, $R_3$ and/or $R_6$, $R_7$ may form a methylenedioxy bridge (—O—CH$_2$—O—); $R_1$, $R_4$, $R_5$ and $R_6$ represent a hydrogen atom; $R_{13}$ may represent either a hydrogen atom, or methyl; to give the product of formula II:

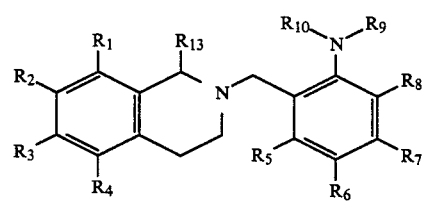

The invention also has as an object a process for preparing derivatives as defined by formula I above, as well as their salts. Compound II may be obtained according to the following diagrams:

1st synthesis diagram

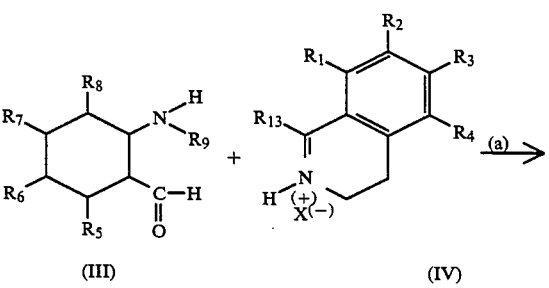

-continued

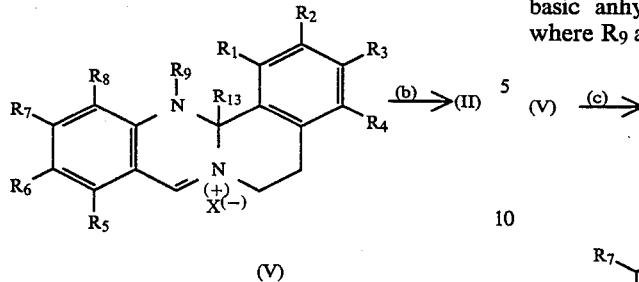

(V)

in which each of the substituents $R_1$, $R_2$, $R_3$, $R_4$, $R_5$, $R_6$, $R_7$ or $R_8$ may represent either a hydrogen atom, a straight or branched chain alkyl group preferably having 1 to 4 carbon atoms, a straight or branched chain alkoxy group preferably having 1 to 4 carbon atoms, a hydroxy group or corresponding esters, a phenoxy group, a benzyloxy group, a methylenedioxy bridge (—O—CH$_2$—O—) when this substituent is connected with an adjacent carbon, a halogen, a nitro group, or an amine function corresponding to primary, secondary, or tertiary amino or quaternary ammonium;

$R_9$ may represent either a hydrogen atom, a straight or branched chain alkyl radical preferably having 1 to 4 carbon atoms, an arylalkyl group, or a group corresponding to primary or secondary or tertiary amino, or quaternary ammonium;

$R_{13}$ may represent either a hydrogen atom or a straight or branched chain alkyl group preferably having 1 to 4 carbon atoms;

$X(-)$ represents the mineral or organic anion associated with the ammonium nitrogen; with the exception of the product where $R_1=R_4=R_5=R_6=R_7=R_8=R_9=R_{13}=H$, $R_2=R_3=OCH_3$ and $X(-)=OH$;

The operating conditions (a) and (b) signify:

(a) Reaction of a 2-aminobenzaldehyde derivative (compound III) with a mineral or organic salt a 3,4-dihydroisoquinoline derivative (compound IV).

(b) Reduction of the obtained 5,6,13,13a-tetrahydro[1,2-b]isoquinoquinazolinium derivative (compound V) dissolved in methanol with sodium borohydride to obtain the product II in base form. Starting from this latter, a bisalt is realized in the presence of an organic or inorganic acid.

2nd synthesis diagram

The compound of structure V is transformed in a basic anhydrous organic medium to derivative VI, where $R_9$ and $R_{13}$ are hydrogen:

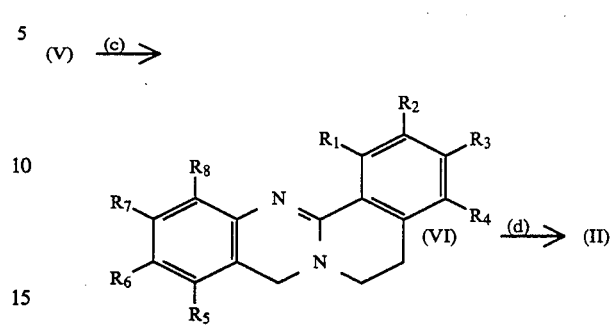

Each of the substituents $R_1$, $R_2$, $R_3$, $R_4$, $R_5$, $R_6$, $R_7$ or $R_8$ may represent either a hydrogen atom, a straight or branched chain alkyl group preferably having 1 to 4 carbon atoms, a straight or branched chain alkoxy group preferably having 1 to 4 carbon atoms, a hydroxy group or corresponding esters, a phenoxy group, a benzyloxy group, a methylenedioxy bridge (—O—CH$_2$—O—) when this substituent is connected with an adjacent carbon, a halogen, a nitro group, or an amine function corresponding to primary or secondary or tertiary amino, or a quaternary ammonium.

The operating conditions (c) and (d) signify:

(c) compound V is transformed to compound VI in basic anhydrous organic medium. Starting from this latter, the salt is realized in the presence of a mineral or organic acid.

(d) Reduction of the obtained base of the compound VI dissolved in methanol with sodium borohydride to obtain product II in the form of base. Starting from this latter, the bisalt is realized in the presence of an organic or inorganic acid.

The structure VI has already been described by William J. Houlihan, Robert E. Manning and Mountain Lakes [Sandoz-Wander, Inc., U.S. Pat. No. 3,542,782 (Cl 260-251)] where $R_1$, $R_4$, $R_5$ and $R_8$ are hydrogen; where each of the substituents $R_2$ or $R_3$ may represent either hydrogen, alkoxy or alkyl; and where of substituents $R_6$ or $R_7$ may represent either hydrogen, fluorine, chlorine, alkyl or alkoxy; and substituents $R_2$, $R_3$ and/or $R_6$, $R_7$ may form a methylenedioxy bridge (—O—CH$_2$—O—).

But the method of preparation according to the invention is different from that published in the prior art.

3rd synthesis diagram

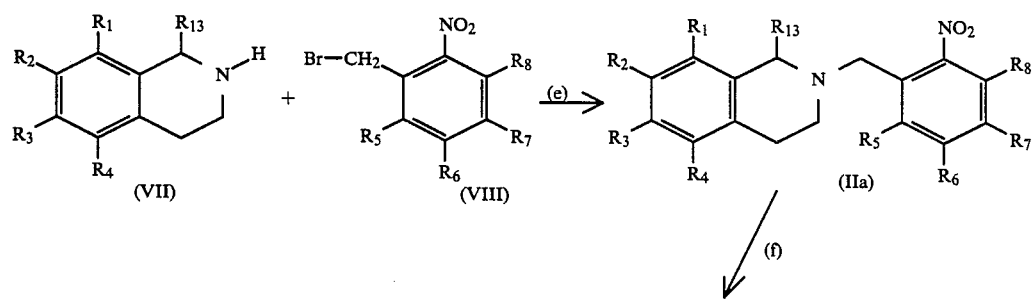

-continued (structural formula IIb with substituents $R_1$, $R_2$, $R_3$, $R_4$, $R_{13}$ on tetrahydroisoquinoline and $NH_2$, $R_5$, $R_6$, $R_7$, $R_8$ on benzyl ring linked via N)

The operating conditions (e) and (f) signify:

(e) Condensation of a 1,2,3,4-tetrahydroisoquinoline derivative (compound VII) with a 2-nitrobenzylbromide derivative (compound VIII) in absolute ethanol in the presence of dry $Na_2CO_3$. Starting from this latter, the salt is realized in the presence of a mineral or organic acid.

(f) Reduction of the base of compound IIa with zinc in acid medium. The base of the product IIb is transformed to the bisalt with a mineral or organic acid.

Each of the substituents $R_1$, $R_2$, $R_3$, $R_4$, $R_5$, $R_6$, $R_7$ or $R_8$ may represent either a hydrogen atom, a straight or branched chain alkyl group preferably having 1 to 4 carbon atoms, a straight or branched chain alkoxy group preferably having 1 to 4 carbon atoms, a hydroxy group or the corresponding esters, a phenoxy group, a benzyloxy group, a methylenedioxy bridge (—O—CH$_2$—O—) when this substituent is connected with an adjacent carbon, a halogen, a nitro group, or an amine function corresponding to primary or secondary or tertiary amino, or quaternary ammonium;

$R_{13}$ may represent either a hydrogen atom or a straight or branched chain alkyl group preferably having 1 to 4 carbon atoms;

with the exclusion of the compound where $R_1=R_4=R_5=R_7=R_8=R_{13}=H$ and $R_2=R_3=OCH_3$ and $R_6=CH_3$.

The derivatives according to the present invention possess interesting pharmacological properties; they have an affinity for α1 and α2 receptors, and are more particularly selective for α2 receptors. The invention thus concerns an α adrenergic activity.

The invention will now be described in greater detail in the following non-limiting examples, among which:

EXAMPLE 1

2-(2-amino-4,5-dimethyoxybenzyl)-6-methoxy-1,2,3,4-tetrahydroisoquinoline (structure II, $R_3=R_6=R_7=OCH_3$ and $R_1=R_2=R_4=R_5=R_8=H$; $R_9=R_{10}=R_{13}=H$)

First step: Synthesis of 5,6,13,13a-tetrahydro-3,10,11-trimethoxy[1,2-b]isoquinoquinazolinium chloride (Structure V, $R_3=R_6=R_7=OCH_3$, $R_1=R_2=R_4=R_5=R_8=R_9=H$; $R_{13}=H$).

In a flask provided with a $CaCl_2$ tube, dissolve 1 g 6-amino-veratraldehyde (0.0055 mole) in 20 ml absolute ethanol. Add 1.1 g 3,4-dihydro-6-methoxyisoquinoline hydrochloride (0.0055 mole) dissolved in a minimum of absolute ethanol. Leave under agitation for one hour. The product precipitates slowly. Filter and wash with absolute ethanol. 1.75 g orange crystals are isolated (yield: 87%).

MP: 161° C.

The structure of the molecule is confirmed by spectral studies: IR (KBr) and NMR (DMSO d6).

Second step: 2-(2-amino-4,5-dimethoxybenzyl)-6-methoxy-1,2,3,4-tetrahydroisoquinoline (Structure II, $R_3=R_6=R_7=OCH_3$ and $R_1=R_2=R_4=R_5=R_8=H$; $R_9=R_{10}=R_{13}=H$).

In an erlenmeyer flask, dissolve 1.75 g 5,6,13,13a-tetrahydro-3,10,11-trimethyoxy[1,2-b]isoquinoquinazolinium chloride in 20 ml methanol. Then add 0.20 g sodium borohydride by successive fractions. Leave in contact under agitation for 30 min. Then add 10 ml water. Extract with chloroform. Dry the chloroform phase with magnesium sulfate. Filter. Evaporate the filtrate. Dissolve the residue with ethyl ether. The product crystalizes. 0.80 g of crystals are isolated (yield: 50%).

MP=100° C.

The structure of the molecule is confirmed by spectral studies: IR ($CHCl_3$) and NMR ($CDCl_3$).

Preparation of the Dihydrochloride

Dissolve 0.80 g of the obtained base in 5 ml chloroform. Add gaseous HCl until saturation. Leave under agitation in an ice bath for 30 min. Add 1 ml anhydrous ethyl ether. The dihydrochloride precipitates. Filter. Dry. The crystals melt at 160° C.

EXAMPLE 2

2-(2-amino-4,5-dimethyoxybenzyl)-6,7-dimethoxy-1,2,3,4-tetrahydroisoquinoline (structure II, $R_2=R_3=R_6=R_7=OCH_3$, $R_1=R_4=R_5=R_8=R_9=H$ and $R_{10}=R_{13}=H$).

First step: Synthesis of 5,6,13,13a-tetrahydro-2,3,10,11-tetramethoxy[1,2-b]isoquinoquinazolium chloride (Structure V, $R_2=R_3=R_6=R_7=OCH_3$, $R_1=R_4=R_5=R_8=R_9=H$ and $R_{13}=H$).

It is produced by reaction of 6-aminoveratraldehyde with 3,4-dihydro-6,7-dimethoxyisoquinoline hydrochloride according to the operating conditions described in the first step of Example 1.

yield: 86%.

MP: 264° C.

The structure of the molecule is confirmed by spectral studies: IR (KBr) and NMR (DMSO d6).

Second step: 2-(2-amino-4,5-dimethoxybenzyl)-6,7-dimethoxy-1,2,3,4-tetrahydroisoquinoline (Structure II, $R_2=R_3=R_6=R_7=OCH_3$, $R_1=R_4=R_5=R_8=R_9=H$ and $R_{10}=R_{13}=H$).

It is produced in a manner analogous to the second step of Example 1.

yield: 55%.

MP: 154° C.

The structure of the molecule is confirmed by spectral studies: IR (KBr) and NMR ($CDCl_3$).

Preparation of the Dihydrochloride

It is produced in a manner analogous to the second step of Example 1.

EXAMPLE 3

2-(2-aminobenzyl)-6,7-dimethoxy-1,2,3,4-tetrahydroisoquinoline (Structure II,
$R_1=R_4=R_5=R_6=R_7=R_8=R_9=R_{10}=R_{13}=H$,
$R_2=R_3=OCH_3$).

First step: Synthesis of 2,3-dimethoxy-5,6,13,13a-tetrahydro[1,2-b]isoquinoquinazolinium chloride (Structure V, $R_2=R_3=OCH_3$, $R_1=R_4=R_5=R_6=R_7=R_8=R_9=H$ and $R_{13}=H$).

In a flask provided with a CaCl$_2$ tube, dissolve 1 g 2-aminobenzaldehyde (0.0083 mole) in 75 ml absolute ethanol. Add 1.88 g 3,4-dihydro-6,7-dimethoxyisoquinoline hydrochloride (0.0083 mole) dissolved in a minimum of absolute ethanol. Heat to boiling for one hour under agitation. Allow to cool. Add 5 ml anhydrous ethyl ether, the product precipitates. Filter. Wash with absolute alcohol.

yield: 55%.
MP=260° C.

The structure of the molecule is confirmed by spectral studies: IR (KBr) and NMR (DMSO d6).

Second step: 2-(2-aminobenzyl)-6,7-dimethoxy-1,2,3,4-tetrahydroisoquinoline (Structure II, $R_1=R_4=R_5=R_6=R_7=R_8=R_9=R_{10}=R_{13}=H$, $R_2=R_3=OCH_3$).

It is produced in a manner analogous to the second step of Example 1.

yield: 50%.
MP=155° C.

The structure of the molecule is confirmed by spectral studies: IR (KBr) and NMR (CDCl$_3$).

Preparation of the Dichlorohydride

It is produced in a manner analogous to the second step of Example 1.

EXAMPLE 4

2-(2-methylamino-4,5-dimethoxybenzyl)-6,7-dimethoxy-1,2,3,4-tetrahydroisoquinoline (Structure II, $R_2=R_3=R_6=R_7=OCH_3$, $R_9=CH_3$ and $R_1=R_4=R_5=R_8=H$; $R_{10}=R_{13}=H$).

First step: Synthesis of 13-methyl-2,3,10,11-tetramethoxy-5,6,13,13a-tetrahydro[1,2-b]isoquinoquinazolinium chloride (Structure V, $R_2=R_3=R_6=R_7=OCH_3$, $R_9=CH_3$, $R_1=R_4=R_5=H$ and $R_8=R_{13}=H$).

In a flask surmounted with a condenser and provided with a CaCl$_2$ tube, dissolve 1 g 2-methylamino-4,5-dimethoxybenzaldehyde (0.0051 mole) in 20 ml absolute ethanol. Then add 1.17 g 3,4-dihydro-6,7-dimethoxyisoquinoline hydrochloride (0.0051 mole). Heat to boiling for ½ hour under agitation. The product precipitates slowly with cooling. Filter and wash with absolute ethanol. 1.20 g orange crystals are isolated (yield: 55%).

MP=264° C.

The structure of the molecule is confirmed by spectral analysis: IR (KBr) and NMR (DMSO d6).

Second step: 2-(2-methylamino-4,5-dimethoxybenzyl)-1,2,3,4-tetrahydro-6,7-dimethyoxyisoquinoline. (Structure II, $R_2=R_3=R_6=R_7=OCH_3$, $R_9=CH_3$ and $R_1=R_4=R_5=R_8=R_{10}=R_{13}=H$).

It is produced in a manner analogous to the second step of Example 1.

yield: 55%.
MP=172° C. (Base).

The structure of the molecule is confirmed by spectral analysis: IR (KBr) and NMR (CDCl$_3$).

Preparation of the Dihydrochloride

It is produced in a manner analogous to the second step of Example 1.

EXAMPLE 5

2-(2-amino-4,5-dimethoxybenzyl)-1,2,3,4-tetrahydroisoquinoline (Structure II, $R_6=R_7=OCH_3$, $R_1=R_2=R_3=R_4=R_5=R_8=H$ and $R_9=R_{10}=R_{13}=H$).

First step: Synthesis of 5,6,13,13a-tetrahydro-10,11-dimethoxy[1,2-b]isoquinoquinazolinium picrate (Structure V, $R_6=R_7=OCH_3$, $R_1=R_2=R_3=R_4=R_5=R_8=R_9=H$ and $R_{13}=H$).

It is produced by reaction of 6-aminoveratraldehyde with 3,4-dihydroisoquinoline picrate according to the operating conditions described in the first step of Example 1.

yield: 95%.
MP: 210° C.

The structure of the molecule is confirmed by spectral studies: IR (KBr) and NMR (CDCl$_3$).

Second step: Synthesis of 5,6,8H-dihydro-10,11-dimethoxy[1,2-b]isoquinoquinazoline. (Structure VI, $R_6=R_7=OCH_3$, $R_1=R_2=R_3=R_4=R_5=R_8=H$).

Dissolve the product obtained from the first step in a minimum of anhydrous pyridine dried with KOH. Heat to boiling under agitation. Then add triethylamine dried with KOH. Leave under agitation for one hour, with boiling. Evaporate under reduced pressure. Dissolve the residue in water alkalinized with soda, and extract with chloroform. Evaporate the chloroform phase dried with magnesium sulfate. Dissolve the residue with a minimum of absolute ethanol and precipitate the product with ethyl ether. Filter and wash.

yield: 65%.
MP: 151° C.

The structure of the molecule is confirmed by spectral studies: IR (KBr) and NMR (CDCl$_3$).

Preparation of the Hydrochloride

Dissolve the obtained base in chloroform. Add gaseous HCl until saturation. Leave under agitation in an ice bath. The hydrochloride precipitates. Filter. Dry.

Third step: 2-(2-amino-4,5-dimethoxybenzyl)-1,2,3,4-tetrahydroisoquinoline. (Structure II, $R_6=R_7=OCH_3$, $R_1=R_2=R_3=R_4=R_5=R_8=H$ and $R_9=R_{10}=R_{13}=H$).

In an erlenmeyer flask, dissolve the base of the product obtained from the preceding second step in methanol, then proceed in a manner analogous to the second step of Example 1; the dihydrochloride is produced in a manner analogous to the second step of Example 1.

yield: 95%.
MP=106° C. (base).

The structure of the molecule is confirmed by spectral studies: IR (KBr) and NMR (CDCl$_3$).

EXAMPLE 6

2-(2-nitro-4-chlorobenzyl)-1,2,3,4-tetrahydroisoquinoline (Structure II, $R_7=Cl$, $R_1=R_2=R_3=R_4=R_5=R_6=R_8=R_{13}=H$, $R_9=R_{10}=O$).

Add 10 ml absolute ethanol to 2.1 g 2-nitro-4-chlorobenzyl bromide, in an erlenmeyer flask. Then add 1.1 g of tetrahydroisoquinoline base. Leave under agitation for one hour. The product precipitates. Filter and wash with absolute alcohol. Recrystalize in alcohol at 95°.
yield: 42%.
MP=101° C.

The structure of the molecule is confirmed by spectral studies: IR (KBr) and NMR (CDCl$_3$).

Preparation of the Hydrochloride

Dissolve the obtained base in chloroform. Add gaseous HCl until saturation. Leave under agitation in an ice bath. The hydrochloride precipitates. Filter. Dry.

EXAMPLE 7

2-(2-amino-4-chlorobenzyl)-1,2,3,4-tetrahydroisoquinoline (Structure II, $R_7=Cl$,
$R_1=R_2=R_3=R_4=R_5=R_6=R_8=H$,
$R_9=R_{10}=R_{13}=H$).

In a flask provided with a condenser, dissolve 1 g 2-(2-nitro-4-chlorobenzyl)-1,2,3,4-tetrahydroisoquinoline in 10 ml 20% hydrochloric acid. Add 1 g powdered zinc. Leave under agitation with reflux for two hours. Hot filter the excess zinc and allow to cool. The dihydrochloride of the amino product precipitates. Filter, alkalinize with dilute soda and extract the base with chloroform. Dry with magnesium sulfate. Evaporate the chloroform.
yield: 72%.
MP=100° C.

The structure of the molecule is confirmed by spectral studies: IR (KBr) and NMR (CDCl$_3$).

EXAMPLE 8

2-(2-nitro-4-chlorobenzyl)-6-methoxy-1,2,3,4-tetrahydroisoquinoline (Structure II,
$R_1=R_2=R_4=R_5=R_6=R_8=R_{13}=H$, $R_3=OCH_3$,
$R_7=Cl$, $R_9=R_{10}=O$).

Add 10 ml absolute ethanol to 2.1 g 2-nitro-4-chlorobenzyl bromide in an erlenmeyer flask. Then add 1.2 g of 6-methoxy-1,2,3,4-tetrahydroisoquinoline base. Leave under agitation for one hour. The product precipitates. Filter and wash with absolute alcohol. Recrystalize in alcohol at 95°.
yield: 45%.
MP=170° C.

The structure of the molecule is confirmed by spectral studies: IR (CDCl$_3$) and NMR (CDCl$_3$).

Preparation of the Hydrochloride

The hydrochloride is obtained in the same manner as described in Example 6.

EXAMPLE 9

2-(2-amino-4-chlorobenzyl)-6-methoxy-1,2,3,4-tetrahydroisoquinoline (Structure II, $R_7=Cl$, $R_3=OCH_3$,
$R_1=R_2=R_4=R_5=R_6=R_8=H$ and
$R_9=R_{10}=R_{13}=H$).

In a flask provided with a condenser, dissolve 1 g 2-(2-nitro-4-chlorobenzyl)-6-methoxy-1,2,3,4-tetrahydroisoquinoline in 10 ml of 20% acetic acid. Add 1 g powdered zinc. Evaporate a maximum of solvent, then extract with chloroform after having alkalinized to a large excess with dilute ammonia. Dry over magnesium sulfate. Evaporate the chloroform. The dihydrochloride is produced in a manner analogous to the second step of Example 1.
yield: 75%.
MP=160° C. (dihydrochloride).

The structure of the molecule is confirmed by spectral studies: IR (KBr) and NMR (DMSO d6).

So as to illustrate the invention, in a non-limiting manner, there will be revealed the results of pharmacological tests that have been conducted with these substances.

So as to facilitate the presentation, the products according to the invention are identified by the code name ISK, and the hydrochlorides of the tested substances, listed hereinafter, are identified by the following code names:

ISK4: 2-(2-amino-4,5-dimethoxybenzyl)-6,7-dimethoxy-1,2,3,4-tetrahydroisoquinoline;
ISK7: 2-(2-amino-4,5-dimethoxybenzyl)-6-methoxy-1,2,3,4-tetrahydroisoquinoline;
ISK17: 2-(2-aminobenzyl)-6,7-dimethoxy-1,2,3,4-tetrahydroisoquinoline;
ISK18: 2-(2-amino-4,5-dimethoxybenzyl)-1,2,3,4-tetrahydroisoquinoline;
ISK23: 2-(2-methylamino-4,5-dimethoxybenzyl)-6,7-dimethoxy-1,2,3,4-tetrahydroisoquinoline;
ISK24: 2-(2-nitro-4-chlorobenzyl)-1,2,3,4-tetrahydroisoquinoline;
ISK25: 2-(2-amino-4-chlorobenzyl)-1,2,3,4-tetrahydroisoquinoline;
ISK31: 2-(2-amino-4-chlorobenzyl)-6-methoxy-1,2,3,4-tetrahydroisoquinoline.

The pharmacological studies effected with the ISK products are described below and explained with reference to the accompanying schematic drawings, in which;

FIG. 3 represents the antagonism between ISK7, yohimbine or prazosine and phenylephrine on the concentration of rat deferent canal.

Figure 1:
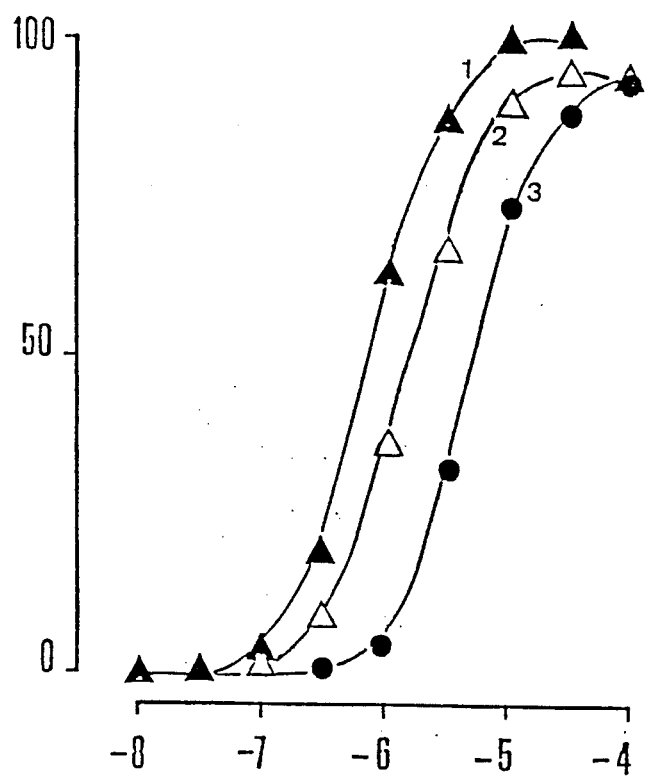
FIG. 1 represents the antagonism of ISK7 relative to BHT 920 (2-amino-6-allyl-5,6,7,8-tetrahydro[4,5-d]thiazolo-4H-azepinedihydrochloride) on rat aorta.

First, the affinity of the products for $\alpha1$ and $\alpha2$ adrenergic receptors of rat cerebral cortex is determined. [$^3$H] prazosine, specific antagonist for $\alpha1$ receptors and [$^3$H] yohimbine, specific antagonist for $\alpha2$ receptors, are utilized as radioactive ligands. The preparation of the cerebral cortex homogenates is made starting from male Wistar rats, age 12 weeks. After decapitation, the brains are rapidly removed and dissected. The tissues are homogenized with the aid of an ultra-turrax in 50 mM of a pH 7.5 Tris-HCl buffer and centrifuged at 40,000 g for ten minutes. The centrifugate is dissolved in buffer and recentrifuged in the same way. All of the operations are carried out at a temperature less than 4° C. The final centrifugate is homogenized in the incubation buffer maintained in melting ice (tris-HCl 50 mM pH 7.5) so as to obtain a final dilution of the cortical tissue of 1/100 (by volume), which corresponds to about 0.5 mg of protein per ml.

1 ml of the tissular suspension is incubated in the presence of a given concentration of radioligand (0.2 nM for [$^3$H] prazosine and 2 nM for [$^3$H] yohimbine) and various concentrations of the molecule in question, in a final volume of 2 ml. (The specific activities of the radioligands are 0.37–1.11 TBq mmol$^{-1}$ for [$^3$H] prazosine and 2.59–3.33 TBq mmol$^{-1}$ for [$^3$H] yohimbine). The tubes are incubated at 25° C. for 30 minutes for [$^3$H]

prazosine, and 20 minutes for [³H] yohimbine, rapidly filtered under vacuum on filters of the tradename Whatman GF/B and made by Whatman. These filters are rinsed 4 times with 5 ml of incubation buffer preserved in ice. The radioactivity retained on the filters is counted by liquid scintillation. The non-specific fixation of the radioactive ligand is evaluated in the presence of 10 μM phentolamine.

Starting from the inhibition curves for the specific fixation of a ligand to its receptor by increasing quantities of a non-radioactive product, the inhibition constant (Ki) of this product is determined. These Ki values are calculated according to Cheng and Prussof (Biochem. Pharmacol. 1973, 22, 3099–3108). In the following table are contained the Ki values (nM) of several compounds, by way of non-limiting example, for the binding sites of [³H] prazosine and [³H] yohimbine.

On the other hand, the compound ISK7 has no affinity for the binding sites of [³H] dexetimide (D2 dopaminergic receptor), [³H] ketanserine (serotonergic receptor), [³H] pyrilamine (H1 histaminic receptor) and [³H] nitrendipine (calcium influx blocking agent).

The ISK products are thus claimed for their selective pharmacological activity for α adrenergic receptors and more particularly for their α2/α1 adrenergic specificity.

$MgSO_4$ 1.19 mM; $KH_2PO_4$ 1.14 mM. The aorta, freed of connective and adipose tissue, is cut in hoops of a length of about 1 mm. Each hoop is installed in a 10 ml organ cell containing Krebs liquid at 37°, oxygenated with an oxygen-carbon dioxide mixture (95% $O_2$ and 5% $CO_2$) and connected to an isometric sensor of tradename Statham and made by Gould Inc., Medical Product Division, under a base tension of 2 g. Recording of the contractions is effected with a polygraph of tradename Beckman and made by Beckman. After a rest period (1 h) interrupted by washings, a first effect-concentration relation is established by studying the contraction provoked by addition in the cell of increasing concentrations of BHT 920. After a new rest period interrupted by washings (30 min.) where the organ returns to the initial tension, the antagonist is placed in contact with the vessel for 10 minutes; the a new effect-concentration relation with BHT 920 is established. In preliminary experiments, it was established that the first and second effect-concentration relation of the agonist are identical in the absence of antagonist. On the other hand, the presence of ISK7 causes a shift to the right of the effect-concentration curve of the agonist, without depression of the maximum. The displacement increases with ISK concentration. This demonstrates that this substance is antagonistic to BHT 920. The apparent dissociation

| Compounds and | | Prazosine [³H] ($K_D = 0.14$ nM) $K_i$ nM | Yohimbine [³H] ($K_D = 10.2$ nM) $K_i$ nM | $K_i\alpha_2/K_i\alpha_1$ |
|---|---|---|---|---|
| ISK₄ (Structure II: | $R_2=R_3=R_6=R_7=OCH_3$ $R_1=R_4=R_5=R_8=H$ $R_9=R_{10}=R_{13}=H$ | 2900 ± 400 | 810 ± 110 | 0,28 |
| ISK₇ (Structure II: | $R_3=R_6=R_7=OCH_3$ $R_1=R_2=R_4=R_5=R_8=H$ $R_9=R_{10}=R_{13}=H$ | 990 ± 50 | 63 ± 20 | 0,06 |
| ISK₁₇ (Structure II: | $R_2=R_3=OCH_3$ $R_1=R_4=R_5=R_6=R_7=H$ $R_8=R_9=R_{10}=R_{13}=H$ | 3400 ± 300 | 1700 ± 300 | 0,50 |
| ISK₁₈ (Structure II: | $R_6=R_7=OCH_3$ $R_1=R_2=R_3=R_4=R_5=H$ $R_8=R_9=R_{10}=R_{13}=H$ | 3220 ± 70 | 220 ± 75 | 0,07 |
| ISK₂₃ (Structure II: | $R_2=R_3=R_6=R_7=OCH_3$ $R_1=R_4=R_5=R_8=H$ $R_9=R_{13}=H$ $R_{10}=CH_3$ | >10 000 | 2665 ± 400 | — |
| ISK₂₄ (Structure II: | $R_7=Cl, R_9=R_{10}=0$ $R_1=R_2=R_3=R_4=H$ $R_5=R_6=R_8=R_{13}=H$ | >30 000 | 2740 ± 1020 | — |
| ISK₂₅ (Structure II: | $R_7=Cl, R_9=R_{10}=H$ $R_1=R_2=R_3=R_4=H$ $R_5=R_6=R_8=R_{13}=H$ | >30 000 | 1400 ± 375 | — |
| ISK₃₁ (Structure II: | $R_7=Cl, R_9=R_{10}=H$ $R_1=R_2=R_4=R_5=H$ $R_6=R_8=R_{13}=H$ $R_3 = OCH_3$ | 1800 ± 330 | 155 ± 35 | 11,6 |
| Prazosine | | 0,15 ± 0.03 | 370 ± 50 | 2467 |
| Yohimbine | | 350 ± 30 | 17 ± 4 | 0.05 |

These results represent the value of at least three experiments ± standard deviation from the mean.

Second, there is demonstrated the antagonism of ISK products relative to the contracture-causing effect of BHT 920 on rat aorta.

The antagonism of ISK7 relative to the contracture-causing effect of BHT 920 (2-amino-6-allyl-5,6,7,8-tetrahydro[4,5-d]thiazolo-4H-azepinedihydrochloride) (α2 adrenergic agonist) on rat aorta is taken as an example. There is antagonism when a substance is capable of partially or totally opposing the effects of an agonistic substance.

Rapidly removed female Wistar rat aorta is received in a Krebs solution containing: NaCl 120 mM; KCl 4.8 mM; $NaHCO_3$ 25 mM; glucose 10 mM; $CaCl_2$ 1.25 mM;

constant of ISK7, calculated from experiments illustrated in FIG. 1 for a competitive antagonism according to Furchgott R. F. (in Catecholamines, ed. by Blaschko and Muscholl, Springer-Verlag, Berlin, 1972, pp. 283-335) is $1.2 \times 10^{-7}$M for the two concentrations employed. This value is comparable to the value of the Ki obtained on the α2 adrenergic binding sites. These results show that ISK7 is an α blocking agent.

FIG. 1 shows the −log (BHT 920) in moles on the abscissa, and the contraction as a percentage of maximum contraction on the ordinate; the curve (1) represents the effect-concentration curve of BHT in the absence of ISK7, and curves (2) and (3) in the presence of $10^{-7}$ and $10^{-6}$ moles of ISK7, respectively. By structural analogy of the ISK products with ISK7, we claim α2 adrenergic antagonistic activity for the derivatives according to the present invention.

Third, *the effect of ISK7 on α1 and α2 adrenergic receptors of isolated rat deferent canal is compared with the reference substances prazosine and yohimbine.*

The effect on α1 type receptors is demonstrated by competitive inhibition of the contraction induced by competitive inhibition of the contraction induced by addition of phenylephrine (a selective α1 agonist) to the surviving liquid, on the α2 type receptors by a competitive antagonism with the inhibiting effect of clonidine (a selective α2 agonist) on the response of the organ to stimulation in an electric field, according to the method described by Starke (Naunyn-Schmiedeberg's Arch. Pharmac., 1972, 275, 11–23). The deferent canals of 12-week old male Wistar rats are removed. Each deferent canal is placed in a 50 ml organ cell filled with a Krebs solution containing: NaCl 118 mM; KCl 4.7 mM; $CaCl_2$ 2.5 mM; $KH_2PO_4$ 1.2 mM; $MgSO_4$ 1.2 mM; $NaHCO_3$ 25 mM; glucose 12.5 mM.

The survival liquid is maintained at 37° C., oxygenated by an oxygen-carbon dioxide mixture (95% $O_2$ and 5% $CO_2$). Each organ is connected to an isometric sensor of tradename Statham, made by Gould Inc., Medical Product Division, under a base tension of 0.5 g. Contractions are recorded by a polygraph of tradename Beckman, made by Beckman. To characterize the α2 blocking effect, the deferent canal is electrically stimulated by rectangular impulses of 2 msec duration, 30 volts, with a frequency of 0.2 Hz delivered by a stimulator of tradename Bioscience (Stimulator 100), made by Palmer. After a rest period of 20–30 minutes, increasing concentrations of clonidine are added to the survival medium over 2 minutes. This permits establishing the relation between the effect and concentration of clonidine. After generating two successive, cumulative effect-concentration curves separated by a rest period of 20 minutes, the antagonist is placed in contact with the isolated organ for 10 minutes and a new effect-concentration relationship is determined. In preliminary experiments, it was established that the second and third effect-concentration relation with the agonist are identical in the absence of antagonist.

To characterize the α1 blocking effect, the organ is stimulated by phenylephrine. Stimulation of the rat deferent canal produces a rapid contractile response (maximum contraction is obtained in 30 seconds). After a rest period of 30 minutes, increasing concentrations of phenylephrine are added in the organ cell over 30 seconds. A first effect-concentration relationship is established. After a washing and a new rest period of 15 mins. wherein the organ returns to the initial tension, a second effect-concentration relationship is effected. The antagonist is placed in contact with the tissue returned to its base tension after washing and a third effect-concentration relationship is determined. In preliminary experiments, it was established that the second and third effect-concentration relationship of the agonist are identical in the absence of antagonist. Quantitative evaluation of the antagonism is effected by calculation of $pA_2$ according to Arunlakshana and Schild (Br. J. Pharmacol. Chemother., 1959, 14, 48–58). The apparent dissociation constant ($K_D$), calculated according to Furchgott, is the relation between the molar concentration of antagonist and the relation of equiactive doses of agonist (in the presence and absence of antagonist) −1. This constant is calculated when determination of $pA_2$ is not possible (when the slope of the Schild relation is different than 1).

Figure 2:
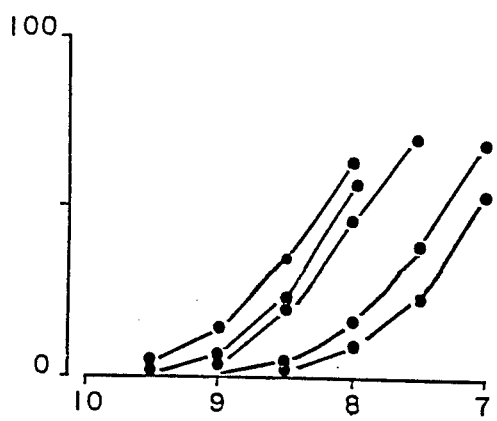
FIG. 2 represents the antagonism between ISK7, yohimbine or prazosine and clonidine on electrically stimulated rat deferent canal.
Figure 2:
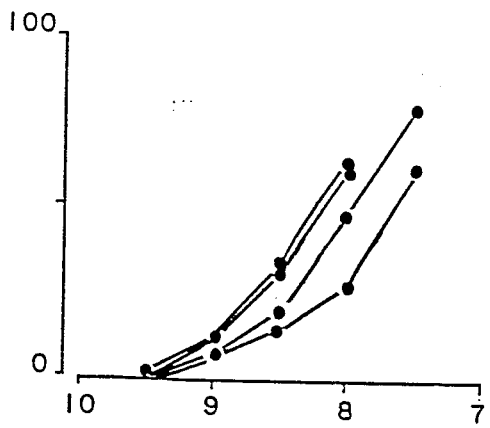
Figure 2:
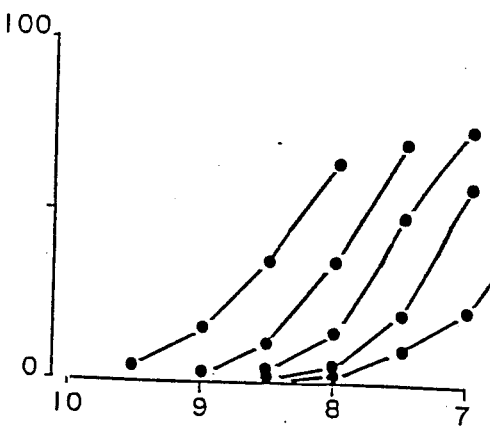

FIG. 2 shows that the inhibiting effect of clonidine on the contractile response of the stimulated deferent canal is antagonized by ISK7 and the reference substances (yohimbine and prazosine). ISK7, yohimbine and prazosine produce a shift toward the right of the effect-concentration curves of agonist without diminution of the maximum effect of this latter. The three diagrams of FIG. 2 represent the antagonism of ISK7 (FIG. 2A, with concentrations of 0; 100; 300; 1000; 3000 nM), prazosine (FIG. 2B, with concentrations 0; 1000; 3000; 10,000 nM) or yohimbine (FIG. 2C, with concentrations 0; 30; 100; 300; 1000 nM) as a function of the −log (clonidine) in moles, on the electrically stimulated rat deferent canal. The effect (inhibition of the contractile response) is expressed as a percentage of the maximum effect. This displacement increases with the concentration of the antagonists.

The $pA_2$ values for the presynaptic α adrenergic receptors of ISK7 and yohimbine are calculated and contained in the table below.

| Substances | Antagonism with clonidine on the response to electric stimulation | | Antagonism with phenylephrine | |
|---|---|---|---|---|
| | $pA_2$ | Slope | $pA_2$ | Slope |
| ISK7 | 6.7 | 1.05 | 5.54 (a) | |
| Yohimbine | 7.59 | 1.15 | 6.08 | 0.85 |
| Prazosine | 5.14 (a) | | 8.34 | 0.99 |

(a) -log of $K_D$; $pA_2$ cannot be calculated because the slope $<<1$

For these two substances, the Schild relation is linear, with a slope not significantly different than 1. In the case of pazosine, the slope of the Schild relation is very different from 1, and the apparent dissociation constant $K_D$ is calculated in this case.

FIG. 3 shows that in the presence of ISK7, yohimbine or prazosine, the effect-concentration curves of phenylephrine are shifted toward the right without depression of the maximum. The three diagrams of FIG. 3 represent −log (phenylephrine) on the abscissa in moles, and on the ordinate the contraction as a percentage of the maximum contraction in the presence, repectively, of ISK7 (FIG. 3A, at concentrations of 0; 1; 3; 10 and 30 μM), yohimbine (FIG. 3B, with concentrations of 0; 3; 10; 30; 100 nM). The (FIG. 3C, with concentrations of 0; 3; 10; 30; 100 nM). The displacement increases with antagonist concentration. The $pA_2$ values are calculated and contained in the table above. The Schild relation is lenar, with a slope of 0.99 for prazosine and 0.85 for yohimbine. In the case of ISK7, the slope of the Schild relation is very different than 1; the apparent dissociation constant $K_D$ has thus been calculated.

The results set forth above demonstrate that ISK7 is a selective, α2 type adrenergic antagonist on isolated rat deferent canal. These results are in accord with those obtained on isolated rat aorta, since the $pA_2$ of ISK7 is respectively 6.7 on dererent canal and 6.9 on aorta. They moreover confirm, with the aid of a pharmacological technique that permits functional characterization of the receptors, the conclusions of the biochemical study of the competition between ISK7 and the α- adrenergic ligands produced with the aid of specific binding techniques.

Specifically, the present invention shows that ISK7 inhibits the effect of α1 adrenergic agonist, phenylephrine, only at concentrations very significantly higher than the concentrations at which it competitively inhibits the effect of α2 selective agonist, clonidine. The α2 blocking activity of ISK7 thus demonstrated is usually interperted as a pre-junctional action manifested by the increase of the inhibition exerted by the activation of the α2 receptors on the libereation of noradrenaline provoked by electrical stimulation of the sympathetic nerve endings.

The therapeutic applications of the invention are those which flow from blockage of α2 adrenergic receptors. For example, it is known that receptors of this nature exist in the central nervous system, in smooth vasular muscles, in blood platelets, in hte endorcinal pancreas, and in the ciliary process.

Blockage of these α2 adrenergic receptors may cause modifications of catecholaminergic transmissions in the central nervous system, a decrease of the vasoconstricting effect off catecholamines in smooth vascular muscles, an inhibition of blood platelet aggregation, a regulation of insulin sercretion by the endocrinal pancreas and consequently a hypoglycemic effect, a decrease of intraocular pressure at the level of the ciliary process.

The corresponding therapeutic indications may especially be mental depression, certain arterial hypertensions, certain hemostasic conditions, certain diabets and treatment of glaucoma. Consequently, the present invention also has an object medicaments, characterized in that they contain the novel 2-(2-aminobenzyl or 2-nitrobenzyl)-1,2,3,4-tetrahydroisoquinoline derivatives of formula I, as active principles. In particular, these medicaments may preferably be used in the following applications:

in mental depression, the active principles act by a modification of catecholaminergic transmissions; in certain arterial hypertensions, the active principles act via inhibition of the vasoconstricting effect of catecholamines;

in certain hemostasic conditions, the active principles inhibit blood platelet aggregation;

in certain diabets, the active principles regulate sercretion of insulin and glycemia;

in glaucoma, the active principles decrease introcular pressure.

In will be understood that the present invention is in no way limited to the indications and applications described. Other indications and applications are possible, as well as modifications to the indications and applications described, without departing whatsoever from the scope of the invention.

We claim:
1. 2-(2-amino-4,5-dimethoxybenzyl)-6-methoxy-1,2,3,4-tetrahydroisoquinoline, or a therapeutically acceptable acid addition salt thereof.
2. A compound which is a member selected from the group consisting of
2-(2-amino4,5-dimethoxyhenzyl)-6,7-dimethoxy-1,2,3,4-tetrahydroisoquinoline;
2-(2-aminobenzyl)-6,7-dimethoxy-1,2,3,4-tetrahydroisoquinoline;
2-(2-amino-4,5-dimethoxybenzyl)-1,2,3,4-tetrahydroisoquinoline;
2-(2-methylamino-4,5-dimethoxybenzyl)-6,7-dimethoxy-1,2,3,4-tetrahydroisoquinoline;
2-(2-nitro-4-chlorobenzyl)-1,2,3,4-tetrahydroisoquinoline;
2-(2-amino-4-chlorobenzyl)-1,2,3,4-tetrahydroisoquinoline;
2-(2-nitro-4-chlorobenzyl)-6-methoxy-1,2,3,4-tetrahydroisoquinoline;
2-(2-amino-4chlorobenxyl)-6-methoxy-1,2,3,4-tetrahydroisoquinoline;
and an acid addition salt thereof.

* * * * *